United States Patent [19]
Lyons et al.

[11] Patent Number: 5,990,348
[45] Date of Patent: Nov. 23, 1999

[54] CONVERSION OF ALKANES TO UNSATURATED CARBOXYLIC ACIDS OVER HETEROPLOY ACIDS SUPPORTED ON POLYOXOMETALLATE SALTS

[75] Inventors: James E. Lyons, Wallingford; Anthony F. Volpe, Lansdale; Paul E. Ellis, Jr., Downingtown; Swati Karmakar, Norristown, all of Pa.

[73] Assignees: Sunoco, Inc.; Rohm and Haas Company, both of Philadelphia, Pa.

[21] Appl. No.: 09/002,845

[22] Filed: Jan. 5, 1998

[51] Int. Cl.[6] .............................. C07C 51/16; C07C 27/10
[52] U.S. Cl. ........................................ 562/549; 562/512.2
[58] Field of Search .................................. 562/549, 512.2

[56] References Cited

U.S. PATENT DOCUMENTS

| | | | |
|---|---|---|---|
| 4,803,187 | 2/1989 | Lyons et al. | 502/200 |
| 4,859,798 | 8/1989 | Lyons et al. | 568/399 |
| 4,898,989 | 2/1990 | Ellis, Jr. et al. | 568/399 |
| 4,916,101 | 4/1990 | Lyons et al. | 502/209 |
| 5,091,354 | 2/1992 | Ellis, Jr. et al. | 502/200 |
| 5,191,116 | 3/1993 | Yamamatsu et al. | 562/549 |
| 5,334,780 | 8/1994 | Shaikh et al. | 568/910 |

FOREIGN PATENT DOCUMENTS

| | | |
|---|---|---|
| 0 418 657 A2 | 3/1991 | European Pat. Off. |
| 0 425 666 B1 | 4/1994 | European Pat. Off. |
| H2-42033 | 2/1990 | Japan . |
| H6-218286 | 8/1994 | Japan . |

OTHER PUBLICATIONS

Pope, et al., Heteropoly and Isopoly Oxometalates, Springer-Verlag, pp. 17–18, and 31–32, New York (1993).

Uemura, et al., "Oxotrimetal Acetato–complexes of Chromium, Manganese, Iron, Cobalt, Rhodium, and Iridium." *J. Chem. Soc. Dalton Trans.*, pp. 2565–2571, (1973).

Finke, et al., "Trisubstituted Heteropolytungstates as Soluble Metal Oxide Analogues 3.[1] Synthesis, Characterization, $^{31}$P, [29]Si, [51]V, and 1 –and 2–D [183]W NMR, Deprotonation, and H[+] Mobility Studies of Organic Solvent Soluble Forms of $H_xSiW_9V_3O_{40}{}^{x-7}$." *J. Amer. Chem. Soc.*, vol. 108, pp. 2947–2960, (1986).

Fernando Ortega, Ph.D., Thesis, Georgetown University, (1982).

Domaille, et al., "Synthesis and [183]W NMR Characterization of Vanadium–Substituted Polyoxometallates Based on B–type $PW_9O_{34}{}^{9-}$ Precursors." *Inorg. Chem.*, vol. 25, pp. 1239–1242, (1986).

M. Ai, "Partial Oxidation of n–Butane with Heteropoly Compound–based Catalysts." *Labo. Resources Utiliz., Tokyo Inst. Tech., Yokohama, Japan, Proceedings of the 18th International Congress on Catalysis, vol. V: Cluster–derived catalysts, Active phase support interactions, Catalysts for synthesis of Chemicals, Vergal Chemie*, vol. 5, pp. V475–V486, Berlin, (1984).

N. Mizuno, et al., "Synthesis of $[PW_9O^{37}\{Fe_{3-x}Ni_x(Oac_3)\}]^{(9-x)-}$ (x=predominantly 1) and Oxidation Catalysis by the Catalyst Precursors." *J. Mol. Cat.*, vol. 88, L125 –31, (1994).

Wu, et al., "Catalytic Behaviour of Metal Ions Located at Different Sites of Heteropoly Compounds." *Catlysis Letters*, vol. 23, pp. 195–205, (1994).

Ueda, et al., "Catalytic Oxidation of Isobutane to Methacrylic acid with molecular Oxygen Over Activated Pyridinium 12–Molybdophosphate." *Cat. Lett.*, vol. 46, pp. 261–265, (1997).

F, Trifiro, "Reactivity of Keggin–type Heteropolycompounds in the Oxidation of Isobutane to Methacrolein and Methacrylic Acid: Reaction Mechanism." *J. Mol. Catal., A*, vol.114, pp. 343–359, (1996).

Mizuno, et al., "Direct Oxidation of Isobutane into Methacrylic Acid and Methacrolein over $Cs_{2.5}Ni_{0.08}$–substituted $H_3Pmo_{12}O_{40}$." *J. Chem. Soc., Chem. Commun.*, pp. 1411–1412, (1994).

Mizuno, et al., "Catalytic Performance of $Cs_{2.5}Fe_{0.08}H_{1.26}PVMo_{11}O_{40}$ for Direct Oxidation of Lower Alkanes." *J. Mol. Catal., A*, vol. 114, pp. 309–317, (1996).

M. Ai, "Oxidation of Propane to Acrylic Acid." *Catalysis Today*, vol.13 (4), pp. 679–684 (Eng.) (1992).

G. Centi, et al., "Selective Oxidation of Light Alkanes: Comparison Between Vanadyl Pyrophosphate and V–Molybdophosphoric Acid." *Catal. Sci. Technol., Proc. Tokyo Conf., 1st Meeting*, pp. 225–230, (1990).

Mizuno, et al., "Pronounced Catalytic Activity of $Fe_{0.08}Cs_{2.5}H_{1.26}PVMo_{11}O_{40}$ for direct oxidation of propane into acrylic acid." *Applied Catalysis A: General*, vol. 128, L165–L170, (1995).

Ueda, et al., "Partial Oxidation of Propane to Acrylic Acid over Reduced Heteropolymolybdate catalysts." *Chemistry Letters*, vol. 541–2, (1995).

Cavani, et al., "Enhancement of Catalytic Activity of the Ammonium/Potassium Salt of 12–Molybdophosphoric Acid by Iron Ion Addition for the Oxidation of Isobutane to Methacrylic Acid." *Catalysis Letters*, vol. 32, pp. 215–226, (1995).

Blake, et al, "Magnetic and Spectroscopic Properties of Some Heterotrinuclear Basic Acetates of Chromium (III), Iron (III), and Divalent Metal Ions." *J. Chem. Soc. Dalton Trans.*, pp. 2509–2520, (1985).

*Primary Examiner*—Samuel Barts
*Assistant Examiner*—Rosalynd Keys
*Attorney, Agent, or Firm*—Pepper Hamilton LLP

[57] ABSTRACT

Alkanes are converted to unsaturated carboxylic acids by contacting an alkane with an oxidizing agent and a heteropolyacid supported on wide pore polyoxometallate salts.

27 Claims, 2 Drawing Sheets

CONVERSION OF ALKANES TO UNSATURATED CARBOXYLIC ACIDS OVER HETEROPLOY ACIDS SUPPORTED ON POLYOXOMETALLATE SALTS

FIELD OF THE INVENTION

This invention relates to compositions comprising wide pore polyoxometallate salts, catalyst compositions derived from supporting heteropolyacids on such salts, methods for their preparation, and the use of heteropolyoacids supported on such salts for the direct catalytic oxidation of alkanes to unsaturated carboxylic acids.

BACKGROUND OF THE INVENTION

Polyoxometallates

Polyoxometallates and heteropolyacids, both in general and those which can be used to prepare some of the catalysts used in our invention, and their preparation are described in Pope et al., *Heteropoly and Isopoly Oxometalates,* Springer-Verlag, New York (1983).

Polyoxometallates and heteropolyacids consist of a polyhedral cage structure or framework bearing a negative charge (e.g., $[PW_{12}O_{40}]^{-3}$) which is balanced by cations that are external to the cage. If the cations are protons, then the compound is a heteropolyacid (HPA) (e.g., $H_3[PW_{12}O_{40}]$). If the cations were not all hydrogen, but either metals such as an alkali metal, potassium, sodium, or lithium, as in $K_3PW_{12}O_{40}$, or ammonium, as in $(NH_4)_3PW_{12}O_{40}$, then it is referred to as a polyoxometallate (POM). In earlier patents, we have used the term "polyoxoanion" to describe compounds in which some or all of the cations are not hydrogen (e.g., $K_3PW_{12}O_{40}$ or $H(VO)[PW_{12}O_{40}]$); in the present case, however, these compounds are referred to as polyoxometallates and the term polyoxoanion is reserved for describing the anionic cage-like portion of the compound (e.g., $[PW_{12}O_{40}]^{-3}$).

As described in Pope et al., supra, heteropolyacids and polyoxometallates are cage-like structures with a primary, generally centrally located atom(s) surrounded by a cage framework, which framework contains a plurality of metal atoms, the same or different, bonded to oxygen atoms. The central element of heteropolyacids and polyoxometallates is different from metal atoms of the framework and is sometimes referred to as the "hetero" element or atom; the condensed coordination elements are referred to as the "framework" elements or metals. The framework metal atoms are ordinarily transition metals. As described by Pope et al., supra, the majority of heteropolyacids and polyoxometallates have a centrally located heteroatom ("X") usually bonded in a tetrahedral fashion through four oxygen atoms to the "framework" metals ("M"). The framework metals, in turn, (i) are usually bonded to the central atom in an octahedral fashion through oxygens ("O"), and (ii) are bonded to four other framework metals through oxygen atoms and (iii) have a sixth non-bridging oxygen atom known as the "terminal oxygen" atom. This can be illustrated as shown below:

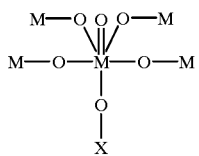

The principal framework metal, M, is effectively limited to only a handful of metals including molybdenum, tungsten, vanadium, niobium and tantalum. According to Pope et al., supra, this is due to the necessary condition that suitable metals have appropriate cation radius and be good oxygen pπ-electron acceptors. Among the successful candidates, molybdenum and tungsten share a common feature; namely, the expansion of valences of their metal cations from four to six. The coincidence of these characteristics allow these metals to form stable heteropolyacids and polyoxometallates.

Conventional heteropolyacids (and polyoxoanions thereof) can be described by the general formula $H_e(X_kM_nO_y)^{-e}$. In this formula, X, the central atom, is frequently phosphorus. However, other suitable central atoms include Group IIIB–VIB elements, such as antimony, silicon and boron. Further, the subscript k is preferably 1, but can be as high as 5. M is molybdenum, tungsten, or vanadium and n will vary from 5–20. The subscript y is usually about 40, but can be as low as 18 or as high as 62. The notation e is the negative charge on the $(X_kM_nO_y)$ polyoxoanion and will vary from case to case, but e is always the number of protons needed to balance the formula. In a typical such heteropolyacid, k=1, n=12 and y=40 as in $H_3PMo_{12}O_{40}$ and the polyoxometallate $K_4PW_{11}VO_{40}$.

As described in Pope et al., supra, heteropolyacids are known to exist in a variety of structures including the Keggin, Dawson and Anderson structures. The different structures correspond to the specific geometry of particular heteropolyacid compositions and vary according to the coordination chemistry and atomic radii of the metals present.

Substituted Polyoxometallates

We have earlier disclosed framework-substituted heteropolyacids and polyoxometallates which demonstrated improved activity for the conversion of alkanes to alcohols. Ellis et al., U.S. Pat. No. 4,898,989, issued Feb. 6, 1990. The improvement in catalyst activity was achieved by replacing certain framework atoms M (and the oxygen atoms doubly bonded to them) with zinc or transition metals or combinations thereof. The M atoms thusly replaced are best shown from the following structure:

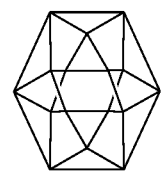

This twelve-cornered polyhedron structure is the metal atom cage-like configuration of a typical Keggin ion heteropolyacid described above. Between any two metal atoms of the framework of the cage is an oxygen atom, not shown, and from each metal atom is also a doubly-bonded oxygen not shown. Each of the metal atoms is bonded through oxygen to the central metal atom, not shown. The structure of polyoxometallates of other kinds (e.g., Dawson ions, Anderson ions) can have different polyhedral structures.

It can be seen from the diagram that eight of the fourteen faces of the above polyhedron are triangular and the other six are four-sided polygons. The M atoms which are replaced, according to our U.S. Pat. No. 4,898,989 patent, supra, are the three metal atoms in a single triangular face, not just any metal atoms as would happen in a random replacement. Another way of characterizing the regioselective, triangular insertion of the substituted metal atoms ("M'"), is that the M' atoms are each joined to each other in the above structural diagram (through oxygen atoms, if the complete structure were shown).

A typical heteropolyacid useful in making the substituted compositions has the formula $H_3PMo_{12}O_{40}$. When three Mo=O units are replaced with, e.g. iron (Fe), the resulting framework substituted heteropolyacid has the formula $H_6PMo_9Fe_3O_{37}$. Thus, the general formula of the regioselectively substituted heteropolyacids described above becomes:

$$H_e(X_kM_nM'_mO_y)^{-e}$$

where k is 1–5, n is 5–19, m is 1–3 and y is 18–61. In this formula, M' comprises zinc or any of the transition metals, namely the Group IIIA–VIII metals of the periodic table. Preferably the transition metal is from Group VIII or the first row of Group IVA–VII, i.e., iron, cobalt, nickel, ruthenium, rhodium, palladium, osmium, iridium, platinum (Group VIII) or titanium, vanadium, chromium, managanese (IVA–VII, first row). Among the more preferred M' metals are iron, manganese, vanadium and combinations of nickel and iron or other transition metal. The three M' atoms do not have to be the same. However, the three M' must be different than the three M atoms replaced.

Preparation of Polyoxometallates

Heteropolyacids are conventionally prepared by dissolving the desired metal oxides in water, adjusting the pH to approximately 1–2 with acid (e.g. HCl) to provide the necessary $H^+$ cations, and then evaporating water until the heteropolyacid precipitates. If polyoxometallate is desired, a salt such as KCl is added. The polyoxometallate ordinarily precipitates without need for an evaporation step. The desired proportion of the metal oxides may vary somewhat from the theoretical amount required for the desired product. The existence of the heteropolyacid structure is confirmed by their characteristic NMR and/or IR spectra, which, as explained in Pope et al., supra, are now known for various heteropolyacids.

In our U.S. Pat. No. 4,803,187, issued Feb. 7, 1989, we taught how to prepare heteropolyacids and polyoxometallates with random substitution of framework metals, such as $H_7(PMo_8V_4O_{40})$; $K_6(SiMo_{11}MnO_{39})$ and $K_5(PW_{11}VO_{40})$. The latter, for example, may be prepared by dissolving 45.0 g of 12-tungstophosphoric acid, $H_3(PMo_{12}O_{40})$, in 105 ml of water. With stirring the pH is adjusted to about 5.2 with potassium bicarbonate. The mixture is then heated to 70/C and 6.0 g of vanadyl sulfate ($VOSO_4$) in 15 ml water is added. The solution is cooled and KCl is added to precipitate the $K_5(PW_{11}VO_{40})$ product.

The preparation of framework-substituted heteropolyacids or polyoxometallates as described in our U.S. Pat. No. 4,803,187 patent, supra, is adequate for random substitution, but will not provide the regiospecific, trilacunary substitution as described in our U.S. Pat. No. 4,898,989 patent, supra; i.e., replacement of three M in a single, triangular face with three M'. In order to achieve the latter, the following generalized procedures may be employed.

The overall procedure involves the reaction of a trilacunary polyoxoanion with a trimetalacetate, the metals of the latter being those to be inserted into the polyoxoanion. Polyoxoanion ("POA") refers to the anionic portion of the compound which is the negatively charged cage without the external protons or cations. The framework substituted polyoxoanion is then converted to the corresponding heteropolyacid if desired. The trilacunary, $Na_9(PW_9O_{34})$, for example is prepared by mixing $Na_2WO_4$ and $H_3PO_4$ in the stoichiometric ratio in water at room temperature for 25 minutes and then slowly acidifyng with 12N HCl to a final pH of 7.1. The $Na_9PW_9O_{34}$ precipitates and is separated. Other trilacunaries are prepared similarly by known analogous procedures.

It is apparent from the above that the $PW_9O_{34}$ in the trilacunary polyoxoanion represents the removal of three O—W=O units from the polyoxoanion and not merely W=O as described for the framework substituted heteropolyacid/polyoxoanion of our prior U.S. Pat. No. 4,803,187. This is merely a matter of satisfying the valences of tungsten (W) in the portion removed. The singly-bonded oxygen in the O—W=O is reinserted when M' is inserted so that the overall effect is the replacement of a M=O with M'; thus changing the number of framework oxygen atoms from 40 to 37.

The trimetal acetates have the general formula $M_3O(CH_3COO)_6(H_2O)_3$ where M is a transition metal or zinc and $M_3$ may be the same or different, e.g., $Fe_2NiO(CH_3COO)_6(H_2O)_3$. They are prepared, e.g., by reaction of appropriate salts. Thus the above diiron-nickel compound is prepared by mixing sodium acetate, iron nitrate, and nickel nitrate in acetic acid/$H_2O$ at room temperature and separating the precipitate. See Blake et al., *J. Chem. Soc. Dalton Trans.*, p. 2509 (1985); and Uemura et al., *J. Chem. Soc. Dalton Trans.*, p. 2565 (1973).

Once the precursors are prepared, the framework substituted heteropolyacid/polyoxometallate is formed by reacting them together. For example, the trilacunary oxoanion $Na_9(PW_9O_{34})$ is dissolved in a pH 6, buffered KOAc/HOAc solution (OAc=acetate). Then an equimolar amount of the trimetal acetate, e.g., $Fe_2NiO(OAc)_6(H_2O)_3$ dissolved in water is added. After initial mixing, the mixture is stirred for one hour at 50° C. and then cooled to room temperature. KCl is added to precipitate the product $K_7(PW_9Fe_2NiO_{37})$. Various preparatory methods are described in Finke et al. *J. Amer. Chem. Soc.*, 108, p. 2947 (1986), F. Ortega, Ph.D. Thesis, Georgetown University (1982), and Domaille et al., *Inorg. Chem.*, 25, 1239–42 (1986).

The polyoxometallate salt can be readily converted to the acid form if desired. This is done by reacting an aqueous solution of the salt, e.g., $K_7PW_9Fe_2NiO_{37}$ at 50° C. for 15 minutes with an aqueous solution containing an excess of tetrabutylammonium bromide. Upon refrigeration at 4° C. overnight, the organic salt, $(nC_4N)_7PW_9Fe_2NiO_{37}$ crystallizes in 70% yield. The organic salt is filtered off and pyrolyzed at 400° C. for 1 hour. It turns into the black solid $H_7PW_9Fe_2NiO_{37}$ as confirmed by IR. The existence of the framework substituted heteropolyacid/polyoxometallate may be confirmed by IR and elemental analysis in known manner.

Regio-disubstituted heteropolyacids and polyoxometallates may be prepared similarly to the procedure described above. A dilacunary species, such as $K_8(SiW_{10}O_{36})$, is reacted at pH 3.8 with a dimeric metal formate, such as $[Cr_2(OH)(O_2CH)](TsO)_3$, where "TsO" is tosylate anion. The product of this reaction after purification is $K_8(SiCr_2W_{10}O_{38})$, where two W=O units have been replaced by two $Cr^{III}$ atoms.

Catalytic Oxidation

As described in Pope et al., supra, heteropolyacids and polyoxometallates have found a variety of applications. In the area of catalysis, they have been used in connection with the oxidation of propylene and isobutylene to acrylic and methacrylic acids, oxidation of aromatic hydrocarbons; olefin polymerization; olefin epoxidation; and hydrodesulfurization processes.

The use of heteropolyacids and polyoxometallates for the catalytic air oxidation of alkanes to alcohols, such as butane to butanol, is also known. See, for example, M. Ai, "Partial Oxidation of n-Butane with Heteropoly Compound-based Catalysts", *Proceedings of the 18th International Congress on Catalysis,* Berlin, 1984, Verlag Chemie, Vol. 5, page 475. In addition, we have previously disclosed the use of heteropolyacids and polyoxometallates under mild reaction conditions for the liquid phase oxidation of alkanes. See, Lyons et al., U.S. Pat. No. 4,803,187, supra. That patent is incorporated by reference herein.

Further, we have previously disclosed modified heteropolyacids and polyoxometallates, methods of preparation, and methods of use for oxidation of alkanes to alcohols. See, Lyons et al., U.S. Pat. No. 4,859,798, issued Aug. 22, 1989; Ellis et al., U.S. Pat. No. 4,898,989, supra; Lyons et al., U.S. Pat. No. 4,916,101, issued Apr. 10, 1990; Ellis et al., U.S. Pat. No. 5,091,354, issued Feb. 25, 1992; and Shaikh et al., U.S. Pat. No. 5,334,780, issued Aug. 2, 1994; each of which is incorporated herein by reference.

We have previously found that substitution of Group VIII and other transition metals as framework elements in a heteropolyacid or polyoxometallate catalyst enhances catalytic oxidation activity for the oxidation of alkanes to alcohols. See, Ellis et al., U.S. Pat. No. 4,898,989, supra; and Ellis et al., U.S. Pat. No. 5,091,354, supra.

Framework-substituted heteropolyacids similar to those described by Ellis et al. and Lyons et al., supra, were subsequently disclosed as catalysts for oxidation of aldehydes, cyclohexene and cyclohexane, and for hydrogen peroxide decomposition. N. Mizuno et al., "Synthesis of $[PW_9O_{37}\{Fe_{3-x}Ni_x(OAc)_3\}]^{(9+x)-}$ (x=predominantly 1) and Oxidation Catalysis by the Catalyst Precursors", *J. Mol. Cat.,* 88, L125–31 (1994), and Wu et al., "Catalytic Behavior of Metal Ions Located at Different Sites of Heteropoly Compounds", *Catalysis Letters,* 23, 195–205 (1994).

Production of Carboxylic Acids

Non-framework substituted polyoxometallates and heteropolyacids are known in the art as catalysts for oxidation of isobutane to methacrylic acid and methacrolein. W. Ueda et al., "Catalytic Oxidation of Isobutane to Methacrylic Acid with Molecular Oxygen over Activated Pyridinium 12-Molybdophosphate", *Cat. Lett.,* 261–265 (1997); N. Mizuno et al., "Catalytic Performance of $Cs_{2.5}Fe_{0.08}H_{1.26}PVMo12O_{40}$ for Direct Oxidation of Lower Alkanes", *J. Mol. Catal.,* A, 114, 309–317 (1996); F. Trifiro, "Reactivity of Keggin-type Heteropolycompounds in the Oxidation of Isobutane to Methacrolein and Methacrylic Acid: Reaction Mechanism", *J. Mol. Catal.,* A, 114, 343–359 (1996); N. Mizuno et al., "Direct Oxidation of Isobutane into Methacrylic Acid and Methacrolein over $Cs_{2.5}Ni_{0.08}$-substituted $H_3PMo_{12}O_{40}$", *J. Chem. Soc., Chem. Commun.,* 1411–1412 (1994); S. Yamamatsu et al., "Process for Producing Methacrylic Acid and Methacrolein", European Patent Specification Publication No. 0 425 666 B1, Application No. 89905775.6 filed May 22, 1989, Date of publication of patent specification Apr. 13, 1994; S. Yamamatsu et al., "Method for the Fabrication of Methacrylic Acid and/or Methacrolein", Japanese Patent Application Public Disclosure No. H2-42034, Feb. 13, 1990; S. Yamamatsu et al., U.S. Pat. No. 5,191,116, issued Mar. 2, 1993; K. Nagai et al., Process for producing methacrylic acid and methacrolein by catalytic oxidation of isobutane", European Patent Application Publication No. 0 418 657 A2, Application No. 90117103.3, filed Sep. 5, 1990 by Sumitomo Chem.Ind.KK (published Mar. 27, 1991).

T. Jinbo et al., "Method for the Manufacture of Acroleic Acid or Acrylic Acid, and Catalysts Used Therein", Japanese Patent Application Public Disclosure No. H6-218286, Aug. 9, 1994, discloses the conversion of propane to acrolein and/or acrylic acid catalyzed by extra-framework metal substituted heteropolyacids; i.e., cation-exchanged heteropolyacids. A single framework mono-substituted heteropolyacid, $H_4PMo_{11}VO_{40}$, showed moderate selectivity for acrylic acid and poor conversion rate.

A heteropolyacid containing ten molybdenum atoms and two vanadium atoms randomly substituted in its framework has been disclosed as catalyzing the oxidation of n-butane to maleic anhydride, acrylic acid and acetic acid. M. Ai, "Partial Oxidation of n-Butane with Heteropoly Compound-based Catalysts", Labo. Resources Utiliz., Tokyo Inst. Tech., Yokohama, Japan, *8th International Congress on Catalysis, Volume V: Cluster-derived catalysts, Active phase support interactions, Catalysts for synthesis of Chemicals,* Verlag Chemie, Berlin, pages V475–V486 (1984).

G. Centi et al., "Selective Oxidation of Light Alkanes: Comparison between Vanadyl Pyrophosphate and V-Molybdophosphoric Acid", Catal.Sci.Technol., *Proc. Tokyo Conf.,* 1st Meeting, 1990, 225–30, 227, disclose that the randomly framework-substituted $H_5PMo_{10}V_2O_{40}$ has been found to be more active than $(VO)_2P_2O_7$ for catalyzing oxidation of propane to acrylic acid. However, the heteropolyacid was inactivated within 1.5 hours. The reported results may suggest that the $H_5PMo_{10}V_2O_{40}$ composition was not functioning as a catalyst, but was rather functioning as a stoichiometric reagent.

Partially exchanged Cs-salts of heteropolyacids have been found to be more active than pure heteropolyacids for catalyzing oxidation of lower alkanes. N. Mizuno et al., "Catalytic Performance of $Cs_{2.5}Fe_{0.08}H_{1.26}PVMo_{11}O_{40}$ for Direct Oxidation of Lower Alkanes", *J. Mol. Catal.,* A, 114, 309–317 (1996).

When a combination of the unsubstituted heteropolyacid, $H_3PMo_{12}O_{40}$, and $V_2O_5$—$P_2O_5$ is used to catalyze oxidation of propane to acrylic acid, this unsubstituted heteropolyacid is disclosed as enhancing the formation of acetic acid byproduct. M. Ai, "Oxidation of Propane to Acrylic Acid", *Catalysis Today,* 13 (4), 679–684 (Eng.) (1992).

N. Mizuno et al., *Applied Catalysis A: General,* 128, L165–L170 (1995), reported that $Fe^{+3}$ or $Ni^{+2}$ exchange for $H^+$; and $V^{+5}$ mono-substitution for $Mo^{+6}$ in $CS_{2.5}H_{0.5}PMo_{12}O_{40}$ enhanced the catalytic activity for direct oxidation of propane to acrylic acid. Of the catalysts tested, $Cs_{2.5}Fe_{0.08}H_{0.5}PMo_{11}VO_{40}$ gave the highest yield of acrylic acid.

Ueda et al., *Chemistry Letters,* 541, 2 (1995), reported that propane was catalytically oxidized to acrylic acid and acetic acid with molecular oxygen over unsubstituted heteropolymolybdophosphoric acids which were treated with pyridine.

Cavani et al., *Catalysis Letters,* 32 215–226 (1995), reported that the addition of iron salts led to a substantial increase in the activity of unsubstituted 12-molybdophosphoric acid for the oxidation of isobutane to methacrylic acid.

The references cited above primarily employed non-framework substituted heteropolyacids as catalysts in manufacture of unsaturated carboxylic acids, for example acrylic acid and methacrylic acid, from alkanes, for example propane and isobutane. As noted, there has also been some use disclosed of heteropolyacids and polyoxometallates with random vanadium substitution of one or two framework metals. The yields and selectivities from the use of vanadium pyrophosphates and/or heteropolyacids, including random, mono- and divanadium-substituted heteropolyacids, described in the cited references was generally below the level required for a practical process. There has been no prior disclosure or use of site-specific, regioselective di-, tri- or multi-substituted heteropolyacids or polyoxometallates for the conversion of alkanes to unsaturated carboxylic acids.

Given the value and industrial importance of acrylic acid and methacrylic acid, it has been recognized that the one-step conversion of alkanes to unsaturated carboxylic acids would be a useful process with important commercial applications, provided that sufficient yield can be obtained. To date, no efficient catalysts have been developed for the commercial production of acrylic acid from propane or methacrylic acid from isobutane. As a result, acrylic acid is manufactured from propylene, a raw material which is over three times more expensive than propane.

The process of the present invention provides such a one-step process for the conversion of alkane to carboxylic acid. The advantages of the process according to the invention are that the higher catalytic activities of the catalysts used in the process allow the process to be carried out at lower temperatures than those used in the prior art, and to obtain higher reaction rates, yields and selectivities than those obtained in the prior art. These advantages make the process more attractive than the prior art processes for practical use and potential commercial interest.

It has been found that the yield and/or selectivity for unsaturated carboxylic acids and nitriles in the partial oxidation of alkanes catalyzed by heteropolyacids and/or polyoxometallates, as such or in combination with vanadium pentoxides, may be increased by substituting oxidation-active metals, for example iron, in Keggin and Dawson structures for metals, for example molybdenum, in the Keggin or Dawson structure to obtain superior catalysts for the direct oxidation of alkanes to unsaturated carboxylic acids, for example, acrylic or methacrylic acids, or for the oxidation of alkanes in the presence of a nitrogen compound to form unsaturated nitriles, for example acrylonitrile or methacrylonitrile.

SUMMARY OF THE INVENTION

The present invention relates to the oxidation of alkanes to unsaturated carboxylic acids or nitriles catalyzed by supported fully or partially protonated polyoxoanions (heteropolyacids (HPAs)) which may also have been promoted or otherwise modified to improve their effectiveness. The support is preferably a wide pore cation salt of a heteropolyacid (polyoxometallate (POM)), for example, a wide pore polyoxometallate salt. The process of the invention is useful, for example, for the conversions of propane to acrylic acid or acrylonitrile, and isobutane to methacrylic acid or methacrylonitrile. In one embodiment, the process of the present invention involves the conversion of alkane to unsaturated carboxylic acid at a temperature in the range of about 225° C. to 450° C. by contacting the alkane with an oxidizing agent in the presence of a supported heteropolyacid catalyst, where the support comprises a wide pore cesium heteropolyoxometallate salt. The process of the invention is also applicable to the conversion of alkanes to unsaturated nitriles.

The invention comprises a process for the conversion of alkanes to unsaturated carboxylic acids which comprises contacting an alkane with an oxidizing agent under oxidation conditions with a heteropolyacid (HPA) supported on a wide-pore polyoxometallate (POM). Thus the catalyst of this process can be defined as a HPA/POM catalyst. The HPA component of the catalysts useful in the process of the present invention has the general formula:

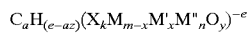

where G is $Cu^{++}$ or $Fe^{+++}$ or an oxy ion of Ti, V, Cr, U, As, Bi, Sb, Nb or La, or is absent; X is a Group IIIB, IVB, VB, VIB or transition element, such as phosphorus, silicon, gallium, aluminum, arsenic, germanium, boron, cobalt, cerium, praseodymium, uranium and thorium; M is molybdenum or tungsten, or combinations thereof; M' is vanadium; M" is independently zinc or a transition metal different from M and M', such as titanium, zirconium, hafnium, vanadium, niobium, tantalum, chromium, molybdenum, tungsten, manganese, rhenium, iron, cobalt, nickel, ruthenium, rhodium, palladium, osmium, iridium, platinum, copper, zinc or combination thereof, z' is the charge on said cation G; k' is 1 to 5, m' is 5 to 17, x' is 0 to 3, n is 0 to 3; y' is 18 to 60; when M is molybdenum, x' is 0 to 3; when M is tungsten, x' is 0 to 6; and e' is the charge of the anion of the polyoxometallate. When M is a combination of molybdenum and tungsten, x' is preferably 0. The support component comprises an insoluble polyoxometallate salt having the formula:

$$C_aH_{(e-az)}(X_kM_{m-x}M'_xM''_nO_y)^{-e}$$

where cation C is selected from the group consisting of potassium, rubidium, cesium, magnesium, calcium, strontium, barium, vanadium, chromium, lanthanum, manganese, iron, cobalt, ruthenium, copper, actinide metal, lanthanide metal, metal oxy ion, ammonium, tetraalkylammonium, pyridinium, quinolinium, protonated aromatic amines and protonated aliphatic amines, or combinations thereof, X is a Group IIIB, IVB, VB, VIB or transition metal; M is molybdenum or tungsten or combinations thereof, M' is vanadium; M" is independently zinc or a transition metal different from M and M', or combination thereof, z is the charge on said cation C; k is 1 to 5, m is 5 to 17, n is 0 to 3, y is 18 to 60; when M is molybdenum, x is 0 to 3; and when M is tungsten, x is 0 to 6. When M is a combination of molybdenum and tungsten, x is preferably 0.

A preferred cation for the support HPA is cesium; for example, $Cs_{3+x}(PMo_{12-x}V_xO_{40})$, where x is 0 to 2. Thus, the HPA/POM catalysts which have been found to be effective have the general formula:

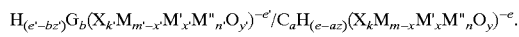

An example of an HPA/POM catalyst is $H_4(PMo_{11}VO_{40})/Cs_3(PMo_{12}O_{40})$.

The conversion process is carried out at a temperature in the range from 225° C. to 450° C., preferably in the range from 275° C. to 400° C. The pressure used in the process of the invention is not critical and may, for example, may be atmospheric pressure or such other pressure as is within the ability of the person skilled in the art to determine.

DETAILED DESCRIPTION OF THE INVENTION

Figure 1:
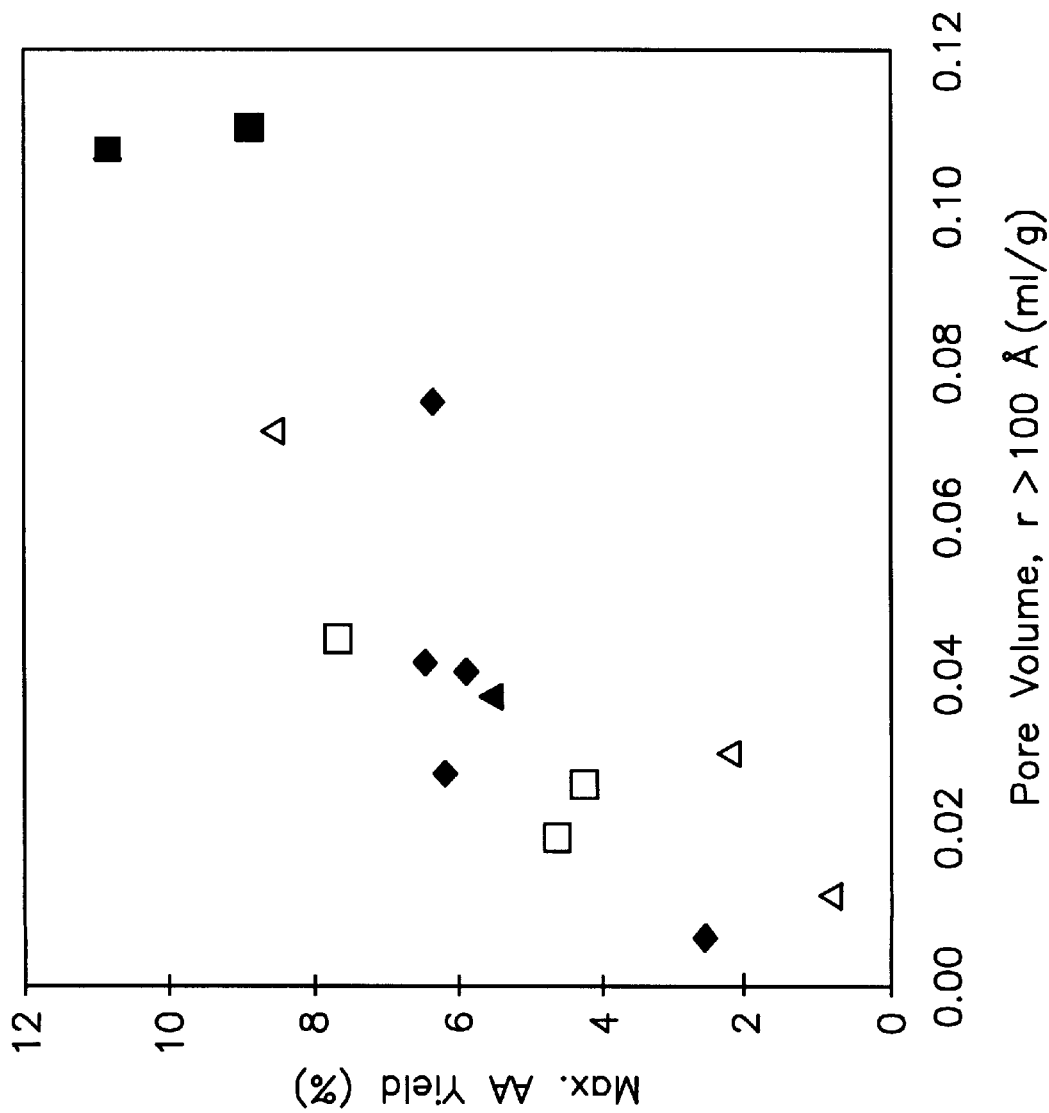
FIG. 1 shows the effect of catalyst support pore volume (in ml/g), for pores with radii greater than 100 Å, on catalyst performance as a function of acrylic acid yield.

The present invention relates to the oxidation of alkanes to unsaturated carboxylic acids or nitriles catalyzed by heteropolyacids (HPAs) supported on wide pore polyoxometallates (POMs) which have been promoted or otherwise

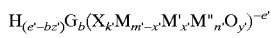

modified to improve their effectiveness. The process of the invention is useful, for example, for the conversions of propane to acrylic acid or acrylonitile and isobutane to methacrylic acid or methacrylonitrile.

Reaction Conditions

The temperature used in the process of the invention is that which favors the formation of unsaturated carboxylic acids or nitriles as reaction products. The conversion process is generally carried out at a temperature in the range from about 225° C. to about 450° C. The process of the invention is typically performed at a temperature of at least about 225° C., and preferably at least about 275° C., and below that which will cause an undesirable level of decomposition of the starting material to carbon oxide and water. Generally, the temperature is not above 450° C., more preferably not above 400° C. Certain catalysts within the scope of the present invention, particularly those HPAs supported on phosphotungstate Keggin ion (e.g., $Cs_3(PW_{12}O_{40})$) have been found to maintain their physical and structural integrity at temperatures up to approximately 500° C. These catalysts in particular may be used in the oxidation process of the present invention at termperatures in the range of 350° C. to 500° C. where propane activation occurs more readily. The determination of the most desirable temperature for a given reaction and given catalyst within the scope of the invention is within the ability of the person skilled in the art.

The pressure used in the process of the invention is not critical. The process may be carried out at atmospheric pressure. Other pressures may be used, and the determination of the most desirable pressure for a given reaction within the scope of the invention is within the ability of the person skilled in the art.

The process of the invention may be carried out in any suitable reactor configuration. For example, the reaction may be performed in a fixed-bed, moving bed, ebullating bed reactor, or other as is within the ability of the person skilled in the art to determine.

The process of the invention is preferably carried out in vapor phase. Preferably, the feedstock is an alkane gas. The reaction may be carried in the presence or absence of steam. An inert gas, such as nitrogen, argon, helium or the like, may also be used. When an inert, diluting gas is used in the process of the invention, determination of the molar ratio of alkane, oxidant, diluting gas and water (steam), if present, in the starting reaction gas mixture is within the ability of the skilled practitioner in the art. Determination of the gas space velocity used in the process of the invention is within the ability of the skilled practioner in the art.

Feedstocks

The alkane starting materials include straight and branched-chain compounds suitable for conversion to unsaturated carboxylic acids or combinations thereof, or to unsaturated nitriles or combinations thereof. Preferred among these are light alkanes comprising three to seven carbon atoms. More preferred feedstocks for the process of the present invention are propane and isobutane which may be oxidized by the process of the present invention to form acrylic acid and methacrylic acid, respectively, or to form acrylonitrile and methacrylonitrile, respectively.

As noted above, the feedstock may comprise a combination of alkanes, preferably $C_3$–$C_7$ alkanes. In addition, the purity of the starting material is not critical, though it is preferable to avoid the presence of compounds which may poison the catalyst. As a result, the feedstock may, in addition to the alkane or alkanes of interest, further comprise methane or ethane as well as impurities such as air or carbon dioxide.

Suitable oxidants for use in the process of the invention comprise air, molecular oxygen and other oxidants, such as nitrogen oxides. Preferred among these are air and molecular oxygen.

In one embodiment of the invention, an alkane is contacted with an oxidizing agent in the presence of a supported heteropolyacid catalyst. For example propane is contacted with an oxidizing agent in the presence of a supported heteropolyacid catalyst according to the invention, to produce acrylic acid. Similarly, isobutane is converted to methacrylic acid. The support comprises a wide pore polyoxometallate salt. The supported heteropolyacid may be substituted as described elsewhere herein.

Catalyst

The catalysts useful in the process of the present invention comprise heteropolyacids supported on wide-pore polyoxometallates. The soluble heteropolyacid component of the catalysts useful in the process of the present invention has the general formula:

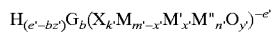

where cation G is $Cu^{++}$ or $Fe^{+++}$ or an oxy ion of Ti, V, Cr, U, As, Bi, Sb, Nb or La, or is absent; X is a Group IIIB, IVB, VB, VIB or transition element, such as phosphorus, silicon, gallium, aluminum, arsenic, germanium, boron, cobalt, cerium, praseodymium, uranium and thorium; M is molybdenum or tungsten, or combinations thereof; M' is vanadium; M" is independently zinc or a transition metal different from M and M', such as titanium, zirconium, hafnium, vanadium, niobium, tantalum, chromium, molybdenum, tungsten, manganese, rhenium, iron, cobalt, nickel, ruthenium, rhodium, palladium, osmium, iridium, platinum, copper, zinc or combination thereof, z' is the charge on said cation G; k' is 1 to 5, m' is 5 to 17, n is 0 to 3; y' is 18 to 60; when M is molybdenum, x' is 0 to 3; when M is tungsten, x' is 0 to 6; b is the number of cations G; and e' is the charge of the anion of the polyoxometallate. When M is a combination of molybdenum and tungsten, x' is preferably 0.

The catalysts used in the process of the invention are heteropolyacids supported on a wide pore polyoxometallate salt. The support comprises an insoluble polyoxometallate salt having the formula:

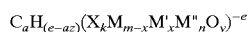

where cation C is selected from the group consisting of potassium, rubidium, cesium; magnesium, calcium, strontium, barium; transition metal, such as vanadium, chromium, lanthanum, manganese, iron, cobalt, ruthenium, copper and the like; actinide metal; lanthanide metal; metal oxy ion, such as oxy ions of vanadium, chromium and uranium and the like; ammonium, tetraalkylammonium, pyridinium, quinolinium, protonated aromatic amines and protonated aliphatic amines, or combinations thereof, X is a Group IIIB, IVB, VB, VIB or transition metal; M is molybdenum or tungsten or combinations thereof, M' is vanadium; M" is independently zinc or a transition metal different from M and M', or combination thereof; z is the charge on said cation C; a is the number of cations C; k is 1 to 5, m is 5 to 17, n is 0 to 3, y is 18 to 60; when M is molybdenum, x is 0 to 3; and when M is tungsten, x is 0 to 6. When M is a combination of molybdenum and tungsten, x is preferably 0. When "az" equals "e", then there are no protons present in the polyoxometallate support.

Suitable cations in the POMs useful in the process of the invention comprise alkali metal, including, not limited to, potassium, sodium, cesium and the like; magnesium, calcium, strontium, barium; transition metal, such as vanadium, chromium, lanthanum, manganese, iron, cobalt, ruthenium, copper and the like; actinide metal, lanthanide metal; metal oxy ion, such as oxy ions of vanadium, chromium and uranium and the like, for example, V=O ("vanadyl"), Cr=O ("chromyl"), U=O ("uranyl") and the like; or other cation such as ammonium, $R_4N^+$ ("tetraalkylammonium") and the like; pyridinium, quinolinium and protonated aromatic amines and protonated aliphatic amines. Of these cations, preferred cations comprise potassium, rubidium, cesium, magnesium, calcium, strontium, barium, lanthanum, ammonium, tetraalkylammonium, pyridinium, quinolinium, protonated aromatic amines and protonated aliphatic amines, or combinations thereof;

A preferred cation for the support POM is cesium; for example, $Cs_{3+x}(PMo_{12-x}V_xO_{40})$, where x is 0 to 3. Other preferred supports include $Cs_3(PMo_{12}O_{40})$, $Cs_4(PMo_{11}VO_{40})$, $Cs_5(PMo_{10}V_2O_{40})$ and $Cs_3(PW_{12}O_{40})$, or combinations thereof. Other suitable supports include wide pore salts, for example wide pore cesium salts of the various substituted polyoxometallates described below and in Lyons et al., U.S. patent application Ser. No. 08/565,206, which is incorporated by reference herein for all purposes.

The support is a porous material having pore volumes in the range from 0.01 to 0.25 ml/g and a pore size distribution in which more than approximately 60% of the pores have a pore radius of greater than or equal to approximately 75 Å, preferably greater than or equal to approximately 100 Å, more preferably greater than or equal to approximately 150 Å, still more preferably greater than or equal to approximately 200 Å. More preferably, the support has pore volumes in the range from 0.05 to 0.25 ml/g and a pore size distribution in which more than approximately 60% of the pores have a pore radius of greater than or equal to approximately 75 Å. In a preferred embodiment, the support material has pore volumes in the range from 0.01 to 0.25 ml/g and a pore size distribution in which more than approximately 80% of the pores have a pore radius of greater than or equal to approximately 200 Å; more preferably, the support material has pore volumes greater than 0.15 ml/g and a pore size distribution in which more than approximately 80% of the pores have a pore radius of greater than or equal to approximately 200 Å.

Preferably, the pores in the support have pore radii of greater than 75 Å and pore volumes greater than 0.05 ml/g; more preferably, the pore radii are greater than 100 Å, and independently, the pore volumes are greater than 0.1 ml/g. It has been found that supports with pore volumes greater than 0.02 ml/g result in catalysts with superior activity, provided the pores are wide (i.e., radii greater than approximately 75 Å). These supported catalysts may be further modified by pretreatment with water and by formation in the presence of vanadyl acetylacetonate or $VOSO_4$.

Typically, the POM support component of the catalyst may be prepared by adding a soluble salt of the desired cation, for example $Cs_2CO_3$ or CsOH or the like for a cesium salt support, to the desired soluble heteropolyacid, for example $H_3(PMo_{12}O_{40})$, to form the insoluble POM, for example $Cs_3(PMo_{12}O_{40})$. The salt solution is preferably added slowly into the heteropolyacid solution to precipitate the cation heteropolymetallate salt. The following reaction (equation 1) exemplifies the process:

$$3Cs_2CO_3 + 2H_3(PMo_{12}O_{40}) \rightarrow 2Cs_3(PMo_{12}O_{40}) + 3H_2O + 2CO_2 \quad (1)$$

The precipitation may be performed at an elevated temperature (e.g., 25–100° C.) and $CO_2$ is evolved during the reaction. The resulting POM salt forms a fine suspension in water and may be evaporated to dryness, for example by roto-evaporation, or by heating at 50° C. or below. The dried material may be calcined (e.g., at 275° C.). POMs having the formula $Cs_aH_{(e-a)}(X_kM_{m-x}M'_xM''_nO_y)^{-e}$ as described more fully herein may be prepared according to this process.

After calcination, the physical properties of the POM salt may be determined, for example the surface area, the pore volume and the pore size distribution (PSD). It has been found that the preparation process can influence these physical characteristics. For example, slow addition of the cation salt to the HPA solution results in a material with few small pores and many large pores. In contrast, rapid addition of the cation salt yields a broad PSD with many small pores and some intermediate and large pores. For the present invention, slow addition to form mainly wide pores is preferable; for example, at a rate of 2 ml/minute, particularly when using solution concentrations of approximately 0.1 mole/liter. More generally, the salt solution may have a concentration in the range from approximately 0.05 to 1 mole/liter, preferably 0.1 to 0.2 mole/liter, and the HPA solution may have a concentration in the range from approximately 0.05 to 1 mole/liter, preferably 0.1 to 0.2 mole/liter, and more preferably 0.1 mole/liter. The solutions may be mixed at a rate in the range from 0.5 to 20 ml/minute, preferably 1 to 10 ml/minute, more preferably 2 mlm/minute. More preferably, particularly for the preparation of large quantities of material, the solutions of the cation salt and the HPA may be added simultaneously to a reaction vessel.

A further factor influencing the PSD was found to be the temperature of the reaction medium during the precipitation step. Precipitation at room temperature yielded a narrow PSD with a median pore radius of about 90 Å, whereas precipitation at 65° C. was found to result in a broader PSD with a greater median pore radius ($\geq 120$ Å). The precipitation step may be carried out at a temperature in the range from approximately 25 to 100° C.; preferably in the range from 50 to 80° C.; more preferably in the range from 60 to 65° C.

Additionally, it has been found that aging of the slurry containing the polyoxometallate salt, followed by slow evaporation to dryness, is beneficial to the production of wide pore materials. Preferably, the slurry is allowed to remain at room temperature or at a temperature in the range from approximately 25° C. to 45° C., preferably 35 to 45° C., for an extended period of time and is then slowly dried. The aging and drying process may extend for a period of 12 to 72 hours or longer. This forms a wide-pore material. Finally, use of excess cation salt (relative to the stoichiometric amount) has been found to promote formation of the desired wide-pore support material. While the support material can be prepared using stoichiometric ratios of starting materials, it is preferred to use an excess of the cation salt.

It has been found that certain POM salts, particularly for example $Cs_3(PMo_{12}O_{40})$, are produced with greater pore sizes and pore volumes than certain other comparably prepared materials, such as $Cs_4(PMo_{11}VO_{40})$, $Cs_3(PW_{12}O_{40})$ and $Cs_3(AsMo_{12}O_{40})$. However, we have developed a novel preparation method involving the simultaneous precipitation of $Cs_3(PMo_{12}O_{40})$ along with the desired POM salt which yields materials with comparable pore sizes and pore volumes to the $Cs_3(PMo_{12}O_{40})$ material.

The following procedure has been found to yield POM salts with comparable desirable pore sizes and pore volumes as $Cs_3(PMo_{12}O_{40})$. According to this process, $Cs_3(PMo_{12}O_{40})$ is in solution with the desired salt of $Cs_3(PM_{12-}$ $_xM'_xO_{40}$) and is simultaneously precipitated with the desired POM salt. Examples of suitable materials for preparation according to this process include, for example, $Cs_4(PMo_{11}VO_{40})$, $Cs_5(PMo_{10}V_2O_{40})$ and $Cs_3(PW_{12}O_{40})$. In order to precipitate the two POM salts simultaneously, a solution of the two HPAs, or two separate solutions of the two HPAs, are slowly mixed with a solution of the salt of the desired cation, for example $Cs_2CO_3$. The solution concentration, the mixing rate, the reaction temperature and the time of drying and aging of the precipitate are the same as that described above. Table IV below shows the pore characteristics of various materials prepared according to this process. It is believed that this process is applicable as well to the preparation of other POM salts described herein.

The heteropolyacids ("HPA") supported on such supports comprise heteropolyacids, which may have been framework-substituted as described below. Likewise, the polyoxometallate ("POM") comprising the support may have been framework-substituted as described below. The substitution may, for example, be monosubstitution, regio-disubstitution or regio-trisubstitution, all of which produce effective compositions for use as the supported HPA and the support POM in the process of the present invention. The catalysts may be further promoted by a variety of means described below. The present invention encompasses unsubstituted and substituted HPAs supported on wide pore salts of unsubstituted and substituted POMs.

In one embodiment, the catalyst, a modified HPA supported on a wide-pore POM as described above, has the general formula:

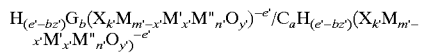

where, in the HPA $H_{(e'-bz')}G_b(X_{k'}M_{m'-x'}M'_{x'}M''_{n'}O_{y'})^{-e'}$, G; the cation, is $Cu^{++}$ or $Fe^{+++}$, or an oxy ion of titanium (Ti), vanadium (V), chromium (Cr), uranium (U), arsenic (As), bismuth (Bi), tin (Sb), niobium (Nb), or lanthanum (La), or is absent; X, the central or hetero atom, is a Group IIIB, IVB, VB, VIB or transition element, such as phosphorus, silicon, gallium, aluminum, arsenic, germanium, boron, cobalt, cerium, praseodymium, uranium and thorium; M, the first framework metal is molybdenum or tungsten or combinations thereof, M' is vanadium substituted for first framework metal M; M'', the second framework metal, is different from M and is independently zinc or a transition metal, such as titanium, zirconium, hafnium, vanadium, niobium, tantalum, chromium, molybdenum, tungsten, manganese, rhenium, iron, cobalt, nickel, ruthenium, rhodium, palladium, osmium, iridium, platinum, copper, zinc or combination thereof, k' is 1 to 5; m' is 5 to 17; n' is 0 to 3; y' is 18 to 59; when M is molybdenum, x' is 0 to 3; and when M is tungsten, x' is 0 to 6; e' is the charge of the anion of the heteropolyacid; and z' is the charge on the cation G; and where, in the POM $C_aH_{(e'-bz')}(X_{k'}M_{m'-x'}M'_{x'}M''_{n'}O_{y'})^{-e'}$, C is selected from the group consisting of potassium, rubidium, cesium, magnesium, calcium, strontium, barium, lanthanum, ammonium, tetraalkylammonium, pyridinium, quinolinium, protonated aromatic amines and protonated aliphatic amines, or combinations thereof; X is a Group IIIB, IVB, VB, VIB or transition metal; M is molybdenum or tungsten or combinations thereof; M' is vanadium; M'' is independently zinc or a transition metal different from M and M', or combination thereof; z is the charge on said cation C; k is 1 to 5, m is 5 to 17, n is 0 to 3; y is 18 to 60, when M is molybdenum, x is 0 to 3; and when M is tungsten, x is 0 to 6; and when "az" equals "e", there are no protons present in the polyoxometallate support. Preferably, when M is a combination of molybdenum and tungsten, x is 0.

In the HPA, the formula (e'-bz') describes the number of protons (H+) present in the heteropolyacid component of the catalyst. At a minimum, (e'-bz') is preferably greater than or equal to 0.1. In one embodiment of the invention, (e'-bz') is greater than or equal to 0.5, in another it is greater than or equal to 1. In some embodiments, bz' equals zero and the number of protons in the HPA is e'.

The catalysts useful in the process of the present invention may be promoted by various means including preparing the HPA in the presence of vanadyl acetylacetonate or the like. In addition, exchange of iron or other transition metals, actinide and lanthanide metals, and other groups, G, has been found to promote the activity of the HPAs of the catalysts used in the process of the invention.

The invention comprises a process for conversion of alkanes to unsaturated carboxylic acids by contacting an alkane with an oxidizing agent under partial oxidation and dehydrogenation conditions with an HPA supported on a POM salt, thereby to convert said alkane to an unsaturated carboxylic acid or an unsaturated nitrile, depending on the oxidant used. The POM or the HPA, or both, may independently comprise (1) at least 9 atoms of a first framework metal or metals comprising molybdenum, tungsten, vanadium or combinations thereof and (2) at least one atom of a second framework metal or metals comprising zinc or a transition metal other than molybdenum, tungsten or vanadium. When there is more than one second framework metal, they may comprise a combination of zinc and the available transition metals.

In one embodiment, the POM and/or the HPA used in the process of the invention comprises 9 to 11 atoms of a first framework metal selected from the group consisting of molydenum, tungsten and vanadium, and 2 to 3 atoms of a second framework metal such as titanium, zirconium, vanadium, niobium, tantalum, chromium, molybdenum, tungsten, manganese, rhenium, iron, cobalt, nickel, ruthenium, rhodium, palladium, osmium, iridium, platinum, copper or zinc, which second metal is zinc or a transition metal different from the first framework metal. The second framework metals (M') are site-specific, regioselective substitutions wherein each M' is bound through an oxygen atom to another M'.

The central or hetero element, X, of the POM and HPA components of the catalyst useful in the process of the present invention is selected from the elements of Group IIIB, IVB, VB, VIB of the Periodic Table or from the transition elements; it may, for example, be phosphorus, silica, aluminum, germanium or the like. In these emdodiments, the first framework element comprises molybdenum, tungsten, vanadium or the like. An example of such heteropolyacid is $H_3PW_{12-n}M'_nO_{40}$, in which phosphorus (P) is the hetero atom and tungsten (W) is the first framework metal and M' is the second framework metal as described below.

The POM or HPA component used in the process of the invention may contain second framework metals which have been substituted into the framework thereof, replacing an equivalent number of the first framework metals. Such substituting metals may, for example, be titanium, zirconium, hafnium, vanadium, niobium, tantalum, chromium, molybdenum, tungsten, manganese, rhenium iron, cobalt, nickel, ruthenium, rhodium, palladium, osmium, iridium, platinum, copper, zinc or combinations thereof. The second framework metal (M') is, by definition, different from the first framework metal (M). When there are more than one M' atoms, each M' is bound through an oxygen atom to another M'.

The atoms which have been replaced in such substitution may be for example molybdenum, tungsten, vanadium or combinations thereof, as disclosed in Ellis and Lyons U.S. Pat. No. 4,898,989, supra. The number of framework atoms replaced may be from 1 to 3 or more, and the substituting metals, which are different from the replaced metal, may each be the same metal, for example iron, or may be different from each other, for example two or three different metal atoms; e.g., one iron atom may replace one tungsten atom; two iron atoms may replace two tungsten atoms; three iron atoms may replace three tungsten atoms; two atoms, different from each other, for example iron and cobalt, may replace two tungsten atoms; three atoms, different from each other, for example iron, cobalt and nickel, may replace three tungsten atoms; two atoms of iron and one atom of cobalt may replace three tungsten atoms; and so on. Replacement of three framework atoms of a POM or HPA by three atoms, different from the framework atom, two of which replacing atoms are selected from the group consisting of iron, chromium, manganese or ruthenium, and the third of which is different from the two just referred to and is a transition metal, is disclosed in Lyons et al., U.S. Pat. No. 5,091,354.

Examples of such HPAs, as disclosed in Lyons et al., U.S. Pat. No. 5,091,354, supra, are $H_6PW_9Fe_3O_{37}\cdot NaN_3$ wherein phosphorus (P) is the hetero atom, tungsten (W) is the first framework metal, and iron (Fe) is the second framework metal; $H_7PW_9Fe_2MO_{37}\cdot NaN_3$, wherein phosphorus (P) is the hetero atom, tungsten (W) is the first framework metal, and iron (Fe) and "M" are the second framework metals, M being variously nickel, manganese, cobalt, zinc; and $H_7PW_9Cr_3O_{37}\cdot NaN_3$, wherein phosphorus (P) is the hetero atom, tungsten (W) is the first framework metal, and chromium (Cr) is the second framework metal. Examples of such heteropolyacids, as disclosed in Hartwell et al., U.S. Pat. No. 4,983,735, supra, are $H_3PW_{10}M_2O_{40}$, where M is titanium, zirconium, niobium, tantalum, manganese, iron, cobalt, nickel or copper. These compositions are useful as the POM and/or HPA component of the supported catalysts of the present invention.

The supported catalyst comprising a heteropolyacid (HPA) supported on POM salt may be prepared, for example, by incipient wetness techniques in which a solution of HPA is sprayed on solid support matrix and then dried, or by adding support material to a solution of HPA and evaporating the solution to dryness. The HPA may be dissolved in water or other solvent, such as acetonitrile. The resulting material is then calcined.

The following process illustrates the catalyst preparation using incipient wetness technique. The amounts of POM support and HPA used are determined on the basis of the total pore volume of the support (typically, 0.13–0.18 ml/g) and the desired catalyst loading (typically about 30 wt. %). The desired amount of HPA is dissolved in solvent (typically water or acetonitrile) which may be as much as approximately 25% in excess of the total pore volume of the support material. After the HPA together with precursors of groups G, if desired, are dissolved, the solution is sprayed evenly on the support material and the supported catalyst is dried, for example at 80° C. for 8 hours when using water, or 50° C. for 8 hours when using acetonitrile. Repeated spraying and drying steps may be used to modify dispersion characteristics. The final supported catalyst material is then calcined. The calcination temperature is preferably between 250° C. and 450° C., and is not so severe as to damage the catalyst structure. The calcination may be performed, for example, at 275° C. for 3 to 6 hours, or at 420° C. for 1 to 2 hours.

The supported HPA catalyst may be pretreated with water which has been found to yield catalysts which give increased acrylic acid production. Preparation of the HPA component of the catalyst in the presence of vanadyl acetylacetonate has also been found to yield catalysts which give increased acrylic acid production when such HPAs are deposited on wide pore POMs.

The HPA may usefully be supported on a catalyst support comprising wide pore POM salt. Supported catalysts with HPA loading of approximately 30 weight percent (i.e., 30 wt. % HPA and 70 wt. % support) may be prepared by standard incipient wetness techniques. Modification of this ratio for purposes of manipulating the activity or other characteristics of the catalyst or the process is within the ability of the practitioner of the art. The amount of HPA and POM support used to prepare the supported catalyst may be varied according to the pore volume of the solid support and the degree of catalyst loading desired. These supported catalysts may be prepared, for example, by slurrying the solid support with a solution of the HPA, or by spraying the HPA dissolved in water onto the dried support or by means known in the art. Preferably, the supported catalyst is dried and calcined prior to use.

In one embodiment of the invention, the supported HPA may be pretreated with water. The catalyst is prepared by exposure to air saturated with water vapor for approximately 48 hours. The hydrated catalyst may comprise about 5 to 30 weight percent water. This pretreatment of the catalyst by hydration was found to enhance catalytic activity.

In one embodiment of the invention, the supported HPA may be prepared in the presence of vanadyl acetylacetonate $(VO(acac)_2)$. The catalyst is prepared by dissolving the HPA and $VO(acac)_2$ and then applying the solution to the support. The supported catalyst is then dried and calcined prior to use.

EXAMPLES

Examples 1 to 3, and the data in Table I, illustrate preparation of HPA compositions and their use as described in Lyons et al., U.S. patent application Ser. No. 08/565,206. The HPAs are used either in crystalized solid form or supported on silica by incipient wetness.

Example 1

We prepared supported and unsupported heteropolyacid catalysts for use in the conversion of propane to acrylic acid. The heteropolyacids used were $H_4PMo_{11}VO_{40}$, $H_5PMo_{10}V_2O_{40}$, and $H_6PMo_9V_3O_{40}$. The first four examples of Table I show results of propane oxidations over solid unsupported 18×35 mesh heteropolyacid pellets.

Prior to catalyst preparation, 18/35 mesh $SiO_2$ pellets were heated in an oven for 6 to 8 hours at an elevated temperature in the range from 300° C. to 500° C. to remove any adsorbed impurities from the surface. Incipient wetness technique was used to support the heteropolyacid on the $SiO_2$ surface.

A given weight of $SiO_2$ pellets was measured and the pore volume of the pellets was calculated from the BET pore volume of the $SiO_2$ support (1.2 ml/g). Based on the desired catalyst loading, e.g. 30 wt %, an appropriate amount of heteropolyacid was weighed in a beaker. The heteropolyacid was dissolved in an approximately 25% excess of water based on the total pore volume of the support since the external surface of the SiO$_2$ pellets also adsorbs water. Acetonitrile could optionally be used to dissolve the heteropolyacid. The water was added to the beaker and the heteropolyacid dissolved with the aid of a magnetic stirrer. The resulting solution was then sprayed evenly on the SiO$_2$ support using a syringe. The supported catalyst was then dried in a furnace at 130° C. for 6 hours, followed by calcination at 325° C. to 350° C. for 3 to 6 hours. When acetonitrile is used to dissolve the heteropolyacid, the drying step was carried out at 50° C.

Example 2

The SiO$_2$-supported heteropolyacids as prepared in Example 1 were further modified by pretreatment with water for use according to one embodiment of the invention.

Supported heteropolyacids H$_4$PMo$_{11}$VO$_{40}$/SiO$_2$, H$_5$PMo$_{10}$V$_2$O$_{40}$/SiO$_2$, and H$_6$PMo$_9$V$_3$O$_{40}$/SiO$_2$ prepared as in Example 1 were placed in a tubular Pyrex reactor furnished with a fritted glass. Air saturated with water vapor at an approximate flow rate of 300 ml/minute was passed through the fixed bed of catalyst for approximately 48 hours. The air was first saturated with water vapor by bubbling it through an impinger containing water at room temperature.

TGA analyses were later carried out to determine the total water content of the pretreated catalysts. The water content of the catalysts was as follows: H$_4$PMo$_{11}$VO$_{40}$/SiO$_2$/H$_2$O—5 wt %; H$_5$PMo$_{10}$V$_2$O$_{40}$/SiO$_2$/H$_2$O—28 wt %, and H$_6$PMo$_9$V$_3$O$_{40}$/SiO$_2$/H$_2$O—27 wt %. As determined by IR and XRD, the passage of water vapor appeared to reconstruct the Keggin structure which had been partially decomposed during calcination and also appeared to improve the dispersion of the heteropolyacid on the SiO$_2$ support.

Example 3

SiO$_2$-supported catalyst as prepared in Example 1 was modified for use in one embodiment of the process of the present invention by preparing the catalyst in the presence of vanadyl sulfate (VOSO$_4$).

Initially, 4.04 g of 18/35 mesh SiO$_2$, which had been predried at 300° C., was weighed in a Pyrex dish. This sample of SiO$_2$ was calculated to have a pore volume of 6 ml.

Since it was desired to produce a catalyst with a final loading of 30 wt %, i.e., 30 wt % catalyst and 70 wt % support, 1.75 g of H(VO)$_2$(PV$_2$Mo$_{10}$O$_{40}$) was needed. The mole ratio of vanadyl to heteropolyacid being 2:1, 1.62 g of H$_5$(PV$_2$Mo$_{10}$O$_{40}$) and 0.41 g of VOSO$_4$.3H$_2$O were used to prepare the H(VO)$_2$(PV$_2$Mo$_{10}$O$_{40}$) catalyst. 0.41 g of VOSO$_4$.3H$_2$O was dissolved in 6 ml of distilled water (corresponding to the pore volume of the support plus 25%) at room temperature using a magnetic stirrer. To that solution, was added 1.62 g of H$_5$(PV$_2$Mo$_{10}$O$_{40}$). The solution was sprayed evenly on the SiO$_2$ using a syringe.

The supported catalyst was dried in a furnace at 130° C. for 6 hours followed by calcination at 325° C. of 3 hours. The IR spectrum of the catalyst showed two peaks at 960 and 860 cm$^{-1}$, which are characteristic of Keggin structures. Additional peaks corresponding to the SiO$_2$ support were also noted.

The data presented in Table I exemplify the effectiveness of various embodiments of the process of the invention utilizing the catalysts prepared as described above. The reaction conditions are set forth in the notes to Table I.

Example 4, and the data of Table II, illustrate preparation of the catalysts of the present invention and their use.

Example 4

The following supported catalysts were prepared according to the process described below:

H$_4$(PMo$_{11}$VO$_{40}$) on Cs$_3$(PMo$_{12}$O$_{40}$),

H$_6$(PMo$_9$V$_3$O$_{40}$) on Cs$_3$(PMo$_{12}$O$_{40}$),

H$_y$Cu$_{0.1}$Sb$_{0.1}$(VO)(PMo$_{12}$O$_{40}$) on Cs$_3$(PMo$_{12}$O$_{40}$),

H$_x$Cu$_{0.1}$As$_{0.1}$(PMo$_{11}$VO$_{40}$) on Cs$_3$(PMo$_{12}$O$_{40}$), and H(VO)(PMo$_{12}$O$_{40}$) on Cs$_3$(PMo$_{12}$O$_{40}$).

The amounts of support and heteropolyacid used are determined on the basis of the total pore volume of the support (typically, 0.13–0.18 mug) and the desired catalyst loading (typically about 30 wt. %). The desired amount of Cs$_3$(PMo$_{12}$O$_{40}$) powder is weighed into a Pyrex dish. The total pore volume of the powder is calculated from the BET pore volume. A certain amount of HPA, based on the desired catalyst loading of approximately 30 wt. %, is placed in a beaker and water is added with stirring. The amount of water is approximately 25% in excess of the total pore volume of the support material. After the HPA is dissolved, the solution is sprayed evenly on the support material with a syringe and the supported catalyst is dried at 80° C. for 8 hours. Repeated spraying and drying steps are used to modify dispersion characteristics. The final supported catalyst material is then calcined at 275° C. for 3 to 6 hours.

Figure 2:
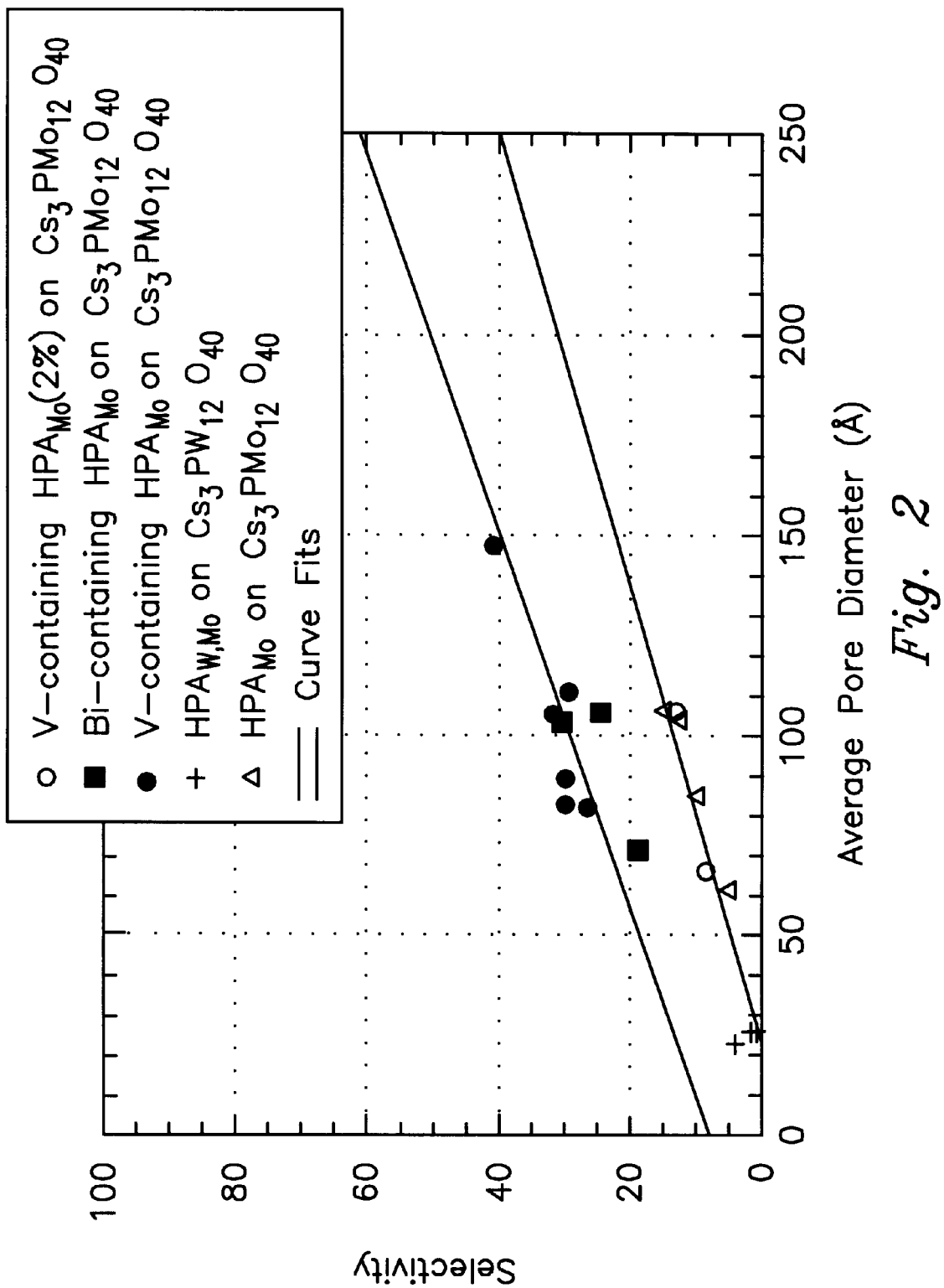
FIG. 2 shows the effect of catalyst support average pore diameter (in Å) on catalyst performance as a function of selectivity for acrylic acid.

The data in FIG. 1 and FIG. 2 show the effectiveness of these supported catalysts in the conversion of propane to acrylic acid; FIG. 1 showing acrylic acid yield as a function of the volume of pores (in ml/g) with radii over 100 Å, and FIG. 2 showing selectivity for acrylic acid as a function of average pore diameter (in Å). The catalysts were prepared as described above.

The data presented in Table II exemplify the effectiveness of various embodiments of the process of the invention utilizing the catalysts prepared as described above. The reaction conditions are set forth in the notes to Table II.

The data presented in Table III illustrate the effect of temperature on the physical properties of phosphomolybdic acids and phosphotungstic acids. The phosphotungstic acids were found to be chemically and structurally stable at high temperatures, including temperatures up to approximately 500° C.

The data presented in Table I were obtained using propane in great excess over the oxidant, air. It is generally preferable for commercial purposes to minimize recycle and reactor size, and, therefore, to run reactions with propane and oxygen ratios close to their stoichiometric ratios (see, equation 2), namely, 1:2.

$$CH_3CH_2CH_3 + 2O_2 \rightarrow CH_2=CHCOOH + 2H_2O \qquad (2)$$

Unsupported HPAs, such as H$_3$PMo$_{12}$O$_{40}$, H$_4$PMo$_{11}$VO$_{40}$, H$_5$PMo$_{10}$V$_2$O$_{40}$ and H$_6$PMo$_{10}$V$_3$O$_{40}$, were found to have short lifetimes of less than or equal to approximately 2 hours and gave turnovers to acrylic acid of less than or equal to approximately 0.1 under stoichiometric conditions. Although superior to unsupported HPAs under conditions of high propane excess, the silica-supported catalysts offered only a minor improvement under practical stoichiometric conditions.

On the other hand, HPAs supported on POMs, such as $Cs_3PMo_{12}O_{40}$, are far more stable than unsupported HPAs under practical stoichiometric conditions, having lifetimes greater than or equal to 200 hours, two orders of magnitude longer than the silica supported HPAs, and three orders of magnitude longer than the unsupported HPAs.

TABLE I

Propane to Acrylic Acid[a]

| Catalyst | SA $m^2/g$ | Acrylic Acid | Acrolein | Propylene | Acetic Acid | $CO_3$ | Acrylic Acid | $C_3=$ |
|---|---|---|---|---|---|---|---|---|
| | | Major Reaction Products, mmoles (6 Hrs.) | | | | | TO (6hrs.)[b] | |
| Crystalline | | | | | | | | |
| $H_3PMo_{12}O_{40}$ | 3.8 | 0.2 | 0.03 | 2.5 | 1.2 | 5.9 | 0.06 | 0.96 |
| $H_4PVMo_{11}O_{40}$ | 3.1 | 0.6 | 0.03 | 8.0 | 1.9 | 11.5 | 0.23 | 3.12 |
| $H_5PV_2Mo_{10}O_{40}$ | 3.5 | 3.1 | 0.2 | 12.7 | 9.1 | 29.3 | 1.06 | 4.35 |
| $H_6PV_3Mo_9O_{40}$ | 1.7 | 0.6 | 0.0 | 2.8 | 6.7 | 11.2 | 0.21 | 2.23 |
| on Silica[c] (30%) | (227.8) | | | | | | | |
| $H_3PMo_{12}O_{40}/SiO_2$ | 158.6 | 0.6 | 0.2 | 6.6 | 2.9 | 18.7 | 1.94 | 20.3 |
| $H_4PVMo_{11}O_{40}/SiO_2$ | 176.2 | 0.7 | 0.1 | 9.3 | 4.9 | 17.6 | 2.30 | 22.4 |
| $H_5PV_2Mo_{10}O_{40}/SiO_2$ | 174.7 | 2.3 | 0.25 | 17.4 | 11.6 | 50.0 | 6.20 | 38.3 |
| $H_6PV_3Mo_9O_{40}/SiO_2$ | | 1.5 | 0.25 | 14.5 | 10.1 | 51.9 | 4.44 | 43.44 |

[a]Propane (42 ml/min), Air (25 ml/min) over catalyst ($C_3/O_2/N_2 = 63/7.5/29.5$).
[b]Moles $C_3^=$ or Acrylic Acid produced in 6 hrs. per mole POM.
[c]4 ml 30% complex on $SiO_2$ contained 0.2 mmoles complex.

TABLE II

ENHANCEMENT OF OXIDATION ACTIVITY OF HETEROPOLYACID CATALYSTS BY SUPPORTING ON A LARGE PORE Cs-SALT OF A PHOSPHOMOLYBDATE OR A PHOSPHOVANADOMOLYBDATE POLYOXOMETALLATE
Surface Area, Pore Volume, PSD, Propane Conversion, AA Yield/Selectivity, etc. of Various POMs supported on $Cs_3PMo_{12}O_{40}$

| HPA Description Support Description | CATALYST DATA | | | | | | | | | REACTOR DATA | | | | | Yield |
|---|---|---|---|---|---|---|---|---|---|---|---|---|---|---|---|
| | SA $m^2/g$ | PV ml/g | MPR Å | Pore Vol. in ml/g for pores with R> | | | | | | Conv % | Carbon Selectivity, % | | | | % |
| | | | | 25Å | 50Å | 75Å | 100Å | 125Å | 150Å | | AA | Acrol | $C_3=$ | COx | |
| $H_4PMo_{11}VO_{40}$ | 24 | 0.042 | 60 | 0.042 | 0.033 | 0.013 | 0.006 | 0.004 | 0.003 | 23.5 | 10.9 | 0.2 | 3.3 | 69.9 | 2.6 |
| $Cs_3PMo_{12}O_{40}$ | 106 | 0.140 | 85 | | | | | | | | | | | | |
| $H_4PMo_{11}VO_{40}$ | 27 | 0.049 | 150 | 0.048 | 0.047 | 0.043 | 0.039 | 0.033 | 0.03 | 27.8 | 21.0 | 0.4 | 4.1 | 54.9 | 5.8 |
| $Cs_3PMo_{12}O_{40}$ | 116 | 0.088 | 160 | | | | | | | | | | | | |
| $H_4PMo_{11}VO_{40}$ | 19 | 0.046 | 140 | 0.044 | 0.044 | 0.044 | 0.040 | 0.032 | 0.022 | 30.7 | 20.9 | 0.3 | 2.8 | 52.6 | 6.4 |
| $Cs_3PMo_{12}O_{40}$ | 59 | 0.148 | 120 | | | | | | | | | | | | |
| $H_4PMo_{11}VO_{40}$ | 14 | 0.062 | 80 | 0.062 | 0.059 | 0.043 | 0.026 | 0.018 | 0.014 | 33.9 | 18.1 | 0.2 | 3.3 | 61.8 | 6.1 |
| $Cs_3PMo_{12}O_{40}$ | 47 | 0.147 | 85 | | | | | | | | | | | | |
| $H_6PMo_9V_3O_{40}$ | 10 | 0.040 | 115 | 0.039 | 0.039 | 0.036 | 0.029 | 0.020 | 0.014 | 27.8 | 8.0 | 0.2 | 4.7 | 71.3 | 2.2 |
| $Cs_3PMo_{12}O_{40}$ | 77 | 0.175 | 165 | | | | | | | | | | | | |
| $H_6PMo_9V_3O_{40}$ | 16 | 0.036 | 70 | 0.035 | 0.029 | 0.017 | 0.011 | 0.009 | 0.007 | 27.2 | 3.1 | 0.2 | 7.0 | 83.8 | 0.8 |
| $Cs_3PMo_{12}O_{40}$ | 106 | 0.140 | 85 | | | | | | | | | | | | |
| $HxCu_{0.1}As_{0.1}PMo_{11}VO_{40}$ | 24 | 0.022 | 160 | 0.022 | 0.021 | 0.020 | 0.018 | 0.016 | 0.014 | 26.7 | 18.7 | 0.6 | 5.4 | 47.4 | 5.0 |
| $Cs_3PMo_{12}O_{40}$ | | | | | | | | | | | | | | | |
| $HxCu_{0.1}As_{0.1}PMo_{11}VO_{40}$ | 24 | 0.045 | 80 | 0.039 | 0.038 | 0.033 | 0.025 | 0.020 | 0.016 | 27.9 | 15.1 | 0.2 | 4.1 | 64.2 | 4.2 |
| $Cs_3PMo_{12}O_{40}$ | 106 | 0.140 | 85 | | | | | | | | | | | | |
| $HxCu_{0.1}As_{0.1}PMo_{11}VO_{40}$ | 10 | 0.056 | 130 | 0.050 | 0.048 | 0.046 | 0.043 | 0.037 | 0.031 | 30.3 | 24.3 | 0.3 | 3.4 | 52.8 | 7.3 |
| $Cs_3PMo_{12}O_{40}$ | 39 | 0.123 | 135 | | | | | | | | | | | | |
| $HyCu_{0.1}Sb_{0.1}(VO)PMo_{12}O_{40}$ | 14 | 0.053 | 100 | | 0.051 | | 0.036 | | | 27.1 | 20.4 | 0.2 | 3.7 | 53.4 | 5.5 |
| $Cs_3PMo_{12}O_{40}$ | 28 | 0.131 | 160 | | | | | | | | | | | | |
| $HyCu_{0.1}Sb_{0.1}(VO)PMo_{12}O_{40}$ | 25 | 0.085 | 140 | 0.081 | 0.080 | 0.078 | 0.070 | 0.061 | 0.051 | 31.9 | 26.9 | 0.3 | 2.7 | 45.9 | 8.6 |
| $Cs_3PMo_{12}O_{40}$ | 39 | 0.123 | 135 | | | | | | | | | | | | |
| $H_2(VO)_{0.5}PMo_{12}O_{40}$ | 22 | 0.111 | 160 | | 0.107 | | 0.097 | | | 44.8 | 22.7 | 0.1 | 0.7 | 48.2 | 10.2 |
| $Cs_3PMo_{12}O_{40}$ | 37 | 0.144 | 200 | | | | | | | | | | | | |
| $H_2(VO)_{0.5}(2,2'bipy)PMo_{12}O_{40}$ | 20 | 0.112 | 170 | | 0.112 | | 0.106 | | | 50.4 | 21.5 | 0.1 | 1.4 | 57.5 | 10.8 |
| $Cs_3PMo_{12}O_{40}$ | 37 | 0.144 | 200 | | | | | | | | | | | | |

TABLE III

Effect of Temperature on the Physical Properties of Cesium Salts of Phosphomolybdic Acids and Phosphotungstic Acids

| Sample Description | Surface Area (m²/g) | Pore Volume (ml/g) | MPR (Å) |
|---|---|---|---|
| Cs$_3$(PMo$_{12}$O$_{40}$) (80%) + Binder, heated in air at 120° C. | 67 | 0.271 | 140 |
| Cs$_3$(PMo$_{12}$O$_{40}$) (80%) + Binder, heated in air at 500° C. | 8 | 0.048 | 150 |
| Cs$_3$(PW$_{12}$O$_{40}$) (80%) + Binder, heated in air at 200° C. | 143 | 0.136 | 35 |
| Cs$_3$(PW$_{12}$O$_{40}$) (80%) + Binder, heated in air at 500° C. | 109 | 0.137 | 35 |
| Cs$_3$(PMo$_{12}$O$_{40}$), heated in air at 275° C. | 106 | 0.161 | 120 |
| Cs$_3$(PMo$_{12}$O$_{40}$), heated in air at 350° C. | 77 | 0.141 | 120 |
| Cs$_3$(PMo$_{12}$O$_{40}$), heated in air at 450° C. | 12 | 0.021 | 100 |

TABLE IV

Improved Pore Characteristics of Cs$_4$(PMo$_{11}$VO$_{40}$) and Cs$_3$(PW$_{12}$O$_{40}$) Precipitated as Mixed Salts

| Sample Description (w/molar ratio) | Surface Area (m²/g) | Pore Volume (ml/g) | MPR (Å) | Pore Volume pores with 50Å | in ml/g for radius> 100Å |
|---|---|---|---|---|---|
| Cs$_3$(PMo$_{12}$O$_{40}$) | 38 | 0.150 | 170 | 0.144 | 0.119 |
| Cs$_3$(PMo$_{12}$O$_{40}$) | 24 | 0.127 | 140 | 0.124 | 0.098 |
| Cs$_4$(PMo$_{11}$VO$_{40}$) | 37 | 0.092 | 75 | 0.080 | 0.010 |
| Cs$_3$(PMo$_{12}$O$_{40}$) | 109 | 0.094 | 60 | 0.067 | 0.006 |
| Cs$_3$(PMo$_{12}$O$_{40}$) + Cs$_4$(PMo$_{11}$VO$_{40}$) (1:1) | 92 | 0.165 | 160 | 0.136 | 0.118 |
| Cs$_3$(PMo$_{12}$O$_{40}$) + Cs$_4$(PMo$_{11}$VO$_{40}$) (1:2) | 29 | 0.129 | 130 | 0.124 | 0.095 |
| Cs$_3$(PMo$_{12}$O$_{40}$) + Cs$_3$(PW$_{12}$O$_{40}$) (1:1) | 105 | 0.146 | 150 | 0.144 | 0.122 |
| Cs$_3$(PMo$_{12}$O$_{40}$) + Cs$_3$(PW$_{12}$O$_{40}$) (1:2) | 103 | 0.116 | 175 | 0.116 | 0.109 |
| Cs$_3$(PMo$_{12}$O$_{40}$) + Cs$_3$(PW$_{12}$O$_{40}$) (1:3) | 104 | 0.112 | 170 | 0.110 | 0.097 |

What is claimed is:

1. A process for the conversion of alkanes to unsaturated carboxylic acids which comprises contacting an alkane with an oxidizing agent and a supported heteropolyacid, wherein said support comprises an insoluble polyoxometallate salt having the formula:

$$C_a H_{(e-az)}(X_k M_{m-x} M'_x M''_n O_y)^{-e}$$

where cation C is selected from the group consisting of potassium, rubidium, cesium, magnesium, calcium, strontium, barium, vanadium, chromium, lanthanum, manganese, iron, cobalt, ruthenium, copper, actinide metal, lanthanide metal, metal oxy ion, ammonium, tetraalkylammonium, pyridinium, quinolinium, protonated aromatic amines and protonated aliphatic amines, or combinations thereof; X is a Group IIIB, IVB, VB, VIB or transition metal; M is molybdenum or tungsten or combinations thereof; M' is vanadium; M" is independently zinc or a transition metal different from M and M', or combination thereof; z is the charge on said cation C; a is the number of cations C; e is the charge of anion $(X_k M_{m-x} M'_x M''_n O_y)$; k is 1 to 5, m is 5 to 17, n is 0 to 3; y is 18 to 60; and when M is molybdenum, x is 0 to 3; and when M is tungsten x is 0 to 6.

2. The process of claim 1 wherein said support comprises cesium salt of heteropolyacid having the formula CS$_e$ (PM$_{12-x}$M'$_x$O$_{40}$)$^{-e}$, where M is molybdenum or tungsten, M' is vanadium, and x is 0 to 3.

3. The process of claim 2 wherein said support is Cs$_3$(PMo$_{12}$O$_{40}$), CS$_4$(PMo$_{11}$VO$_{40}$), CS$_5$(PMo$_{10}$V$_2$O$_{40}$) or Cs$_3$(PW$_{12}$O$_{40}$), or combinations thereof.

4. The process of claim 1 wherein said cation is potassium, rubidium, cesium, magnesium, calcium, strontium, barium, lanthanum, ammonium, tetraalkylammonium, pyridinium, quinolinium, protonated aromatic amines or protonated aliphatic amines, or combinations thereof.

5. The process of claim 1 wherein "a", the number of cations, is greater than or equal to 2 when z is 1.

6. The process of claim 1 wherein said support is a porous material with pores which material has a pore volume in the range from 0.01 to 0.25 ml/g and a pore size distribution in which more than approximately 60% of said pores have a pore radius of greater than or equal to approximately 75 Å.

7. The process of claim 6 wherein more than approximately 60% of said pores have a pore radius greater than or equal to approximately 100 Å.

8. The process of claim 7 wherein more than approximately 60% of said pores have a pore radius greater than or equal to approximately 150 Å.

9. The process of claim 8 wherein more than approximately 60% of said pores have a pore radius greater than or equal to approximately 200 Å.

10. The process of claim 1 wherein said support is a porous material with pores which material has a pore volume in the range from 0.01 to 0.25 ml/g and a pore size distribution in which more than approximately 80% of said pores have a pore radius of greater than or equal to approximately 200 Å.

11. The process of claim 1 wherein said support is a porous material with pores which material has a pore volume in the range from 0.05 to 0.25 ml/g and a pore size distribution in which more than approximately 60% of said pores have a pore radius of greater than or equal to approximately 75 Å.

12. The process of claim 1 wherein said support is a porous material with pores which material has a pore volume in the range from 0.15 to 0.25 ml/g and a pore size distribution in which more than approximately 80% of said pores have a pore radius of greater than or equal to approximately 200 Å.

13. The process of claim 1 wherein said heteropolyacid comprises a soluble heteropolyacid having the formula:

$$H_{(e'-bz')}G_b(X_{k'}M_{m'-x'}M'_{x'}M''_{n'}O_{y'})^{-e'}$$

where G is Cu$^{++}$ or Fe$^{+++}$ or an oxy ion of Ti, V, Cr, U, As, Bi, Sb, Nb or La, or is absent; X is a Group IIIB, IVB, VB, VIB or transition metal; M is molybdenum or tungsten or combinations thereof; M' is vanadium; M" is independently zinc or a transition metal different from M and M', or combination thereof; z' is the charge on said cation G; e' is the charge of anion $(X_{k'}M_{m'-x'}M'_{x'}M''_{n'}O_{y'})$; b is the number of cations G; k' is 1 to 5, m' is 5 to 17, x' is 0 to 3, n is 0 to 3 and y' is 18 to 60.

14. The process of claim 13 where (e'−bz') is greater than or equal to 0.1.

15. The process of claim 14 where (e'−bz') is greater than or equal to 0.5.

16. The process of claim 15 where (e'−bz') is greater than or equal to 1.

17. The process of claim 13 wherein said cation G comprises a metal oxo moiety.

18. The process of claim 17 wherein said metal oxo moiety comprises V=O, Cr=O or U=O, or combinations thereof.

19. The process of claim 13 wherein G is (V=O).

20. The process of claim 1 wherein said heteropolyacid comprises:
   (a) at least 9 atoms of a first framework metal or metals consisting of molybdenum, tungsten, vanadium and combinations thereof, and
   (b) at least one atom of a second framework metal or metals consisting of titanium, zirconium, hafnium, niobium, tantalum, chromium, manganese, rhenium, iron, cobalt, nickel, ruthenium, rhodium, palladium, osmium, iridium, platinum, copper and zinc and combinations thereof.

21. The process of claim 1 wherein said catalyst comprises a heteropolyacid having the formula $H_{(e'-bz')}G_b(X_kM_{m'-x'}M'_{x'}M''_{n'}O_{y'})^{-e'}$ on a polyoxometallate support having the formula $C_aH_{(e-az)}(X_kM_{m-x}M'_xM''_nO_y)^{-e}$, where
   (a) in said formula of said heteropolyacid, G is $Cu^{++}$ or $Fe^{+++}$ or an oxy ion of Ti, V, Cr, U, As, Bi, Sb, Nb or La, or is absent; X is a Group IIIB, IVB, VB, VIB or transition metal; M is molybdenum or tungsten or combinations thereof; M' is vanadium; M'' is independently zinc or a transition metal different from M and M', or combination thereof; z' is the charge on said cation G; e' is the charge of anion $(X_kM_{m'-x'}M'_{x'}M''_{n'}O_{y'})$; b is the number of cations G; k' is 1 to 5, m' is 5 to 17, x' is 0 to 3, n' is 0 to 3 and y' is 18 to 60; and
   (b) in said formula of said polyoxometallate, cation C is selected from the group consisting of potassium, rubidium, cesium, magnesium, calcium, strontium, barium, lanthanum, ammonium, tetraalkylammonium, pyridinium, quinolinium, protonated aromatic amines and protonated aliphatic amines, or combinations thereof; X is a Group IIIB, IVB, VB, VIB or transition metal; M is molybdenum or tungsten or combinations thereof; M' is vanadium; M'' is independently zinc or a transition metal different from M and M', or combination thereof; z is the charge on said cation C; a is the number of cations C; e is the charge of anion $(X_kM_{m-x}M'_xM''_nO_y)$; k is 1 to 5, m is 5 to 17, x is 0 to 3, n is 0 to 3 and y is 18 to 60; and
   (c) said support is a porous material with pores, which material has pore volumes in the range from 0.01 to 0.25 ml/g and a pore size distribution in which more than approximately 60% of said pores have a pore radius of greater than or equal to approximately 75 Å.

22. A process according to claim 1 wherein said alkane comprises light alkane comprising three to seven carbon atoms or combinations thereof.

23. A process according to claim 22 wherein said alkane comprises propane and said product comprises acrylic acid.

24. A process according to claim 22 wherein said alkane comprises isobutane and said product comprises methacrylic acid.

25. A process according to claim 1 wherein said conversion is carried out at a temperature in the range from about 225° C. to about 450° C.

26. A process according to claim 25 wherein said temperature is in the range from about 275° C. to about 400° C.

27. A process according to claim 1 wherein said oxidant is air, molecular oxygen or a nitrogen oxide.

* * * * *

UNITED STATES PATENT AND TRADEMARK OFFICE
CERTIFICATE OF CORRECTION

PATENT NO. : 5,990,348
DATED : November 23, 1999
INVENTOR(S) : Lyons et al.

It is certified that error appears in the above-identified patent and that said Letters Patent is hereby corrected as shown below:

On the Title Page:
    item [54], delete "Heteroploy" and insert -- Heteropoly -- therefor.
    item [75], after "Anthony F. Volpe" insert --,Jr.--.

Column 1, line 3, delete "Heteroploy" and insert -- Heteropoly -- therefor.

Column 3, line 50, delete " U.S. Patent No."

Column 3, line 53, delete " U.S. Patent No."

Column 5, line 43, delete "$Cs_{2.5}Fe_{0.08}H_{1.26}PVMo12O_{40}$" and insert -- $Cs_{2.5}Fe_{0.08}H_{1.26}PVMo_{12}O_{40}$ -- therefor.

Column 18, line 20, delete "(typically, 0.13-0.18mug)" and insert -- (typically, 0.13-0.18ml/g) -- therefor.

UNITED STATES PATENT AND TRADEMARK OFFICE
CERTIFICATE OF CORRECTION

PATENT NO. : 5,990,348
DATED : November 23, 1999
INVENTOR(S) : Lyons et al.

It is certified that error appears in the above-identified patent and that said Letters Patent is hereby corrected as shown below:

In the Claims:

Column 22, Claim number 3, line 2, delete "$CS_4(PMo_{11}VO_{40})$" and insert -- $Cs_4(PMo_{11}VO_{40})$ -- therefor.

Column 22, Claim number 3, line 2, delete "$CS_5(PMo_{10}V_2O_{40})$" and insert -- $Cs_5(PMo_{10}V_2O_{40})$ -- therefor.

Signed and Sealed this

Nineteenth Day of December, 2000

Attest:

Q. TODD DICKINSON

*Attesting Officer*          *Commissioner of Patents and Trademarks*